United States Patent

Shiobara et al.

[11] Patent Number: 5,250,637
[45] Date of Patent: Oct. 5, 1993

[54] SEMICONDUCTOR ENCAPSULATING EPOXY RESIN COMPOSITIONS AND SEMICONDUCTOR DEVICES

[75] Inventors: Toshio Shiobara, Annaka; Kazutoshi Tomiyoshi; Yasuo Tarumi, both of Takasaki; Hiromasa Yamaguchi, Annaka, all of Japan

[73] Assignee: Shin-Etsu Chemical Co., Ltd., Tokyo, Japan

[21] Appl. No.: 981,209

[22] Filed: Nov. 25, 1992

[30] Foreign Application Priority Data

Nov. 25, 1991 [JP] Japan .................. 3-335610

[51] Int. Cl.$^5$ .......................... C08F 283/10
[52] U.S. Cl. .................. 525/487; 525/482; 525/527; 528/103; 528/402
[58] Field of Search ............ 525/482, 487, 527; 528/103, 402

[56] References Cited

U.S. PATENT DOCUMENTS

| | | | |
|---|---|---|---|
| 4,042,550 | 8/1977 | Tuller et al. | 523/457 |
| 4,122,246 | 10/1978 | Sierawski | 528/32 |
| 4,156,046 | 5/1979 | Lien et al. | 524/560 |
| 5,141,802 | 8/1992 | Parrinello et al. | 525/132 |

Primary Examiner—John C. Bleutge
Assistant Examiner—Randy Gulakowski
Attorney, Agent, or Firm—Birch, Stewart, Kolasch & Birch

[57] ABSTRACT

An epoxy resin composition comprising an epoxy resin, a curing agent and an inorganic filler is adapted for semiconductor encapsulation. A fluorinated organic silicon compound is blended in the composition as a coupling agent whereby the composition is improved in adhesion and moisture resistance.

15 Claims, 1 Drawing Sheet

SEMICONDUCTOR ENCAPSULATING EPOXY RESIN COMPOSITIONS AND SEMICONDUCTOR DEVICES

BACKGROUND OF THE INVENTION

1. Field of the Invention

This invention relates to a semiconductor encapsulating epoxy resin composition which cures into products having improved adhesion and moisture resistance and semiconductor devices encapsulated with such cured products.

2. Prior Art

Most advanced semiconductor devices are of the resin encapsulation type which is advantageous in large scale manufacture and thus offers low cost products as compared with the prior art ceramic and can sealed types. Prominent among the encapsulating resins are epoxy resins having excellent electrical and physical properties.

Semiconductor devices encapsulated with resins, typically epoxy resins, however, are less resistant against humidity as compared with the ceramic and can sealed ones and often suffer from entry of water through the resin-frame interface.

Also, ionic impurities including hydrolyzable chlorine are left in encapsulating resins. These impurities interact with water to increase the current leakage of semiconductor devices and cause corrosion of aluminum electrodes, both leading to a lowering of reliability.

Many attempts were made for eliminating the defects associated with the relatively low moisture resistance of epoxy resin-encapsulated semiconductor devices. For example, it was proposed to remove ionic impurities from encapsulating materials and to add thereto an additive capable of trapping ionic impurities. However, it was substantially impossible in practice to ensure complete removal or trapping of ionic impurities. These approaches failed to attain the intended purposes.

Another known approach for improving the moisture resistance of encapsulating resins is to blend silane coupling agents. The known silane coupling agents for use in epoxy resin compositions for encapsulating semiconductor devices are epoxy silanes, mercapto silanes, amine silanes and unsaturated hydrocarbon silanes. Typical of the mercapto silanes is 3-mercaptopropyltrimethoxysilane which gives off an offensive odor and is undesired for practical use. One exemplary amine silane is N-(2-aminoethyl)-3-aminopropylmethyldimethoxysilane which detracts from the shelf stability of resin compositions containing it. The unsaturated hydrocarbon silanes include, for example, vinyltriethoxysilane and 3-methacryloxypropyltrimethoxysilane which are free of a functional group reactive with phenol-curable epoxy resins and thus cannot fully exert their function as a coupling agent. Useful examples of the epoxy silane are 3-glycidoxypropyltrimethoxysilane and 2-(3,4-epoxycyclohexyl)ethyltrimethoxysilane which are free of the above-mentioned problems, but insufficient in adhesion and moisture resistance improvement.

Therefore, an object of the present invention is to provide a semiconductor encapsulating epoxy resin composition having improved adhesion and moisture resistance, especially moisture resistance after a moisture absorption and soldering test. Another object of the present invention is to provide a semiconductor device encapsulated with such an epoxy resin composition in cured state.

SUMMARY OF THE INVENTION

The present invention is addressed to an epoxy resin composition for semiconductor encapsulation comprising an epoxy resin, a curing agent, and an inorganic filler. To the composition is added a fluorinated organic silicon compound of the formula:

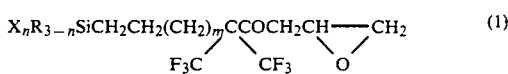

wherein X is a hydrolyzable group, R is a substituted or unsubstituted monovalent hydrocarbon group, n is an integer of 1 to 3, and m is equal to 0 or 1. The resulting epoxy resin composition is effective for the encapsulation of semiconductor devices of any type including DIP, QFP, SOJ, SOP and PLCC types. Semiconductor devices encapsulated with the present composition is improved in adhesion and moisture resistance, especially moisture resistance after a moisture absorption and soldering test.

More particularly, the fluorinated organic silicon compound of formula (1) has fluorine atoms in its molecule and thus exhibits water repellency. It has low surface energy so that it well wets such members as silicon chips and lead frames during encapsulation of semiconductor devices and thus helps the composition adhere to the members. Therefore the epoxy resin composition containing the compound cures into products having excellent sealing properties including moisture resistance.

DETAILED DESCRIPTION OF THE INVENTION

Figure 1:
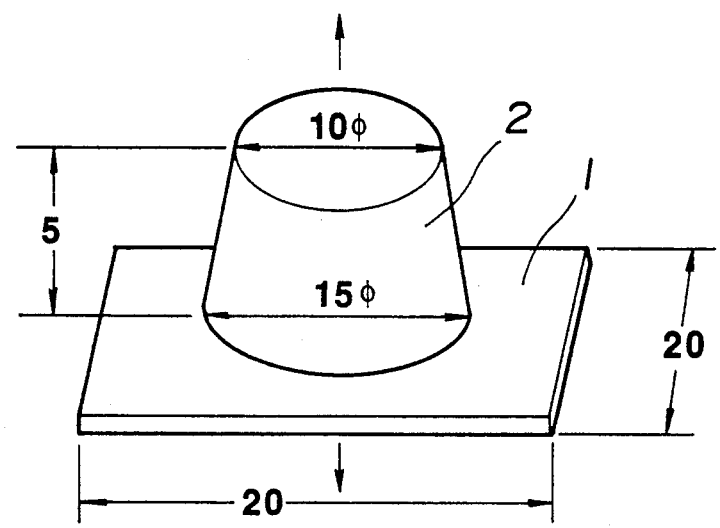
FIG. 1 illustrates how to measure a pulling force to separate an encapsulating resin from a frame.

The epoxy resin used in the semiconductor encapsulating epoxy resin composition according to the present invention is an epoxy resin having at least two epoxy groups in a molecule. Examples include glycidyl ether type epoxy resins such as bisphenol-A type epoxy resins, phenol novolak type epoxy resins, and allyl phenol novolak type epoxy resins; triphenol alkane type epoxy resins and polymers thereof; naphthalene type epoxy resins, biphenyl type epoxy resins, dicyclopentadiene type epoxy resins, phenol aralkyl type epoxy resins, glycidyl ester type epoxy resins, cycloaliphatic epoxy resins, heterocyclic epoxy resins, and halogenated epoxy resins alone or in admixture of two or more.

The curing agent may be selected in accordance with a particular type of epoxy resin. For example, amine curing agents, acid anhydride curing agents and phenol functional curing agents may be used. Among others, the phenol functional curing agents are desirable when the molding and moisture resistance of the composition are taken into account. Examples of the phenol functional curing agent include phenol novolak resins, resol type phenol resins, triphenolalkane type resins, naphthol type resins, biphenyl type resins, and phenol aralkyl resins alone or in admixture of two or more.

The curing agent is added in a sufficient amount to cause the epoxy resin to cure. Thus the amount of curing agent is not critical. In an exemplary system using a phenol functional curing agent, it is preferably added such that the molar ratio of epoxy group in the epoxy resin to phenolic hydroxyl group in the curing agent is in the range of from ½ to 3/2.

A curing promoter may be blended in the epoxy resin composition of the invention for promoting the reaction between the epoxy resin and the curing agent. The curing promoters used herein include imidazoles, cycloamidine derivatives such as 1,8-diazabicyclo-(5.4.0) undecene (DBU), and phosphine derivatives such as triphenylphosphine, and tertiary amines alone or in admixture. The amount of the curing promoter added is not critical although it is preferably added in an amount of 0.01 to 5 parts, more preferably 0.2 to 3 parts by weight per 100 parts by weight of the total of the epoxy resin and curing agent.

The inorganic filler may be selected from those commonly used for epoxy resins. A typical filler is ground quartz. Ground quartz is available as crystalline silica and fused silica and may take any form including crushed form, spherical form, and submicron particulate form. A quartz powder in which the content of coarse particles having a size of more than 75 μm is reduced to below 0.3% by weight of the entire powder is preferred because it minimizes the local stresses applied to semiconductor elements. If necessary or desired, fillers other than silica may be used. Such other useful fillers include talc, mica, clay, kaolin, calcium carbonate, alumina, zinc oxide, baryta, glass balloons, glass fibers, aluminum hydroxide, calcium hydroxide, asbestos, titanium oxide, iron oxide, and silicon nitride. The inorganic filler may be surface treated with silane coupling agents prior to blending.

The filler content may be properly selected. Preferably the filler is used in an amount of about 50 to about 800 parts, especially about 100 to about 650 parts by weight per 100 parts by weight of the total of the epoxy resin and curing agent. Smaller amounts of the filler would be less effective for reducing internal stresses whereas compositions loaded with larger amounts of the filler would become less flowing and thus difficult to mold.

To the epoxy resin composition is added a fluorinated organic silicon compound of formula (1).

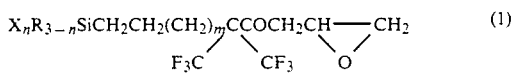
(1)

In the formula, X is a hydrolyzable group, R is a substituted or unsubstituted monovalent hydrocarbon group, n is an integer of 1 to 3, and m is equal to 0 or 1.

The hydrolyzable group represented by X is preferably selected from $OR^1$ and $NR^2R^3$. $R^1$ is an alkyl group having 1 to 10 carbon atoms such as methyl, ethyl, n-propyl, i-propyl and n-butyl groups, a fluoroalkyl group having 3 to 15 carbon atoms such as a trifluoropropyl group, an acyl group such as acetyl and propionyl groups, or an alkenyl group having 2 to 5 carbon atoms such as an isopropenyl group. $R^2$ and $R^3$ are alkyl groups having 1 to 10 carbon atoms such as methyl, ethyl and isopropyl groups, and they may be identical or different.

R is a substituted or unsubstituted monovalent hydrocarbon group, for example, an alkyl group having 1 to 10 carbon atoms such as methyl, ethyl, n-butyl, t-butyl, n-hexyl and cyclohexyl groups, an alkenyl group having 2 to 10 carbon atoms such as vinyl and allyl groups, an aryl group having 6 to 10 carbon atoms such as phenyl and tolyl groups, an aralkyl group having 7 to 15 carbon atoms such as benzyl and phenylethyl groups, and a fluoroalkyl group having 3 to 15 carbon atoms such as a trifluoropropyl group.

Preferred are those compounds of formula (1) wherein X is a lower alkoxy group such as methoxy, ethoxy and isopropenoxy groups and R is a lower alkyl group such as methyl. Most preferred are the fluorinated organic silicon compounds of formulae (1a), (1b) and (1c) shown below.

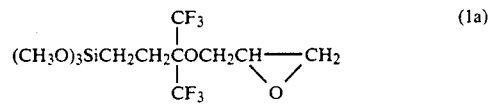
(1a)

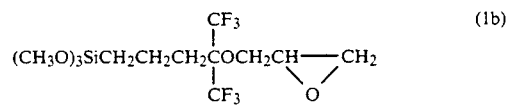
(1b)

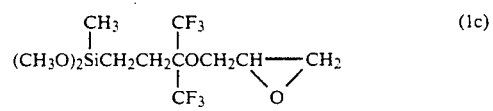
(1c)

The fluorinated organic silicon compounds of formula (1) are novel compounds. They may be synthesized by effecting addition reaction between a fluorinated unsaturated glycidyl ether of formula (2) and a hydrosilane of formula (3) in the presence of a transition metal catalyst in accordance with a process as disclosed in Japanese Patent Application No. 214671/1991.

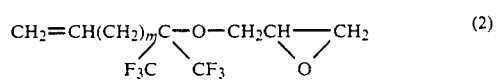
(2)

$$X_nR_{3-n}SiH \tag{3}$$

In these formulae, X, R, n and m are as defined above. The catalyst used herein is a transition metal such as Pt, Rh and Pd or a salt or complex thereof, with rhodium complexes being preferred. Exemplary rhodium complexes are $Rh(CH_2COCHCOCH_2)_3$, $Rh(PPh_3)_3Cl$, $RH(PPh_3)_3Br$, $Rh(PPh_3)_2(CO)Cl$, and $Rh_2(OAc)_4$.

Moreover, the fluorinated unsaturated glycidyl ethers of formula (2) are also novel. They may be prepared by reacting a corresponding alcohol and epichlorohydrin in a two phase system consisting of a basic aqueous phase and an organic phase using a phase transfer catalyst in the form of a quaternary ammonium salt or quaternary phosphonium salt in accordance with the following reaction scheme.

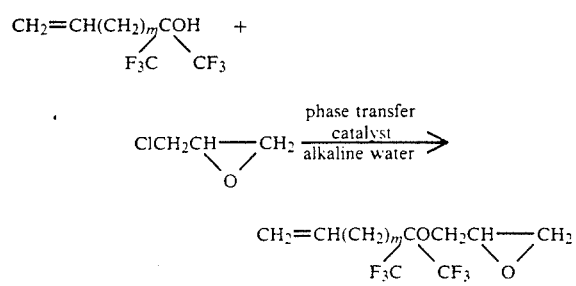

It is not critical how to add the fluorinated organic silicon compound of formyla (1) to the epoxy resin composition. For example, it may be added by integral blending or by blending an inorganic filler having the compound of formula (1) attached to a surface thereof.

The amount of the fluorinated organic silicon compound of formula (1) added may be selected from a wide range although it is preferably blended in amount of 0.05 to 10 parts, more preferably 0.5 to 3 parts by weight per 100 parts by weight of the total of the epoxy resin and curing agent. Less than 0.05 parts on this basis of the compound would be less effective for improving moisture resistance whereas with more than 10 parts of the compound, cured products would have a lower glass transition temperature and the compound could bleed out at the cured product surface.

Besides adding the fluorinated organic silicon compounds of formula (1) as a coupling agent, the composition of the present invention may contain another coupling agent such as γ-glycidoxypropyltrimethoxysilane, if necessary.

For the purpose of reducing stresses, silicone polymers and thermoplastic polymers may be blended in the epoxy resin composition. The addition of these polymers is effective in significantly reducing the occurrence of package cracks in a thermal shock test. The silicone polymers include silicone fluids, resins and rubbers having an epoxy, amino, carboxyl, hydroxyl, vinyl or other group, as well as copolymers of these silicone polymers with organic polymers such as phenol novolak resins and epoxidized phenol novolak resins. Silicone rubber and gel in fine powder form may also be used. The thermoplastic polymers include MBS resins, butyral resins, and aromatic polyester resins.

Preferably, these silicone polymers or thermoplastic polymers are blended in an amount of about 1 to 50 parts by weight per 100 parts by weight of the total of the epoxy resin and curing agent.

The epoxy resin composition of the invention may contain any desired other additive if desired. For example, mold release agents such as wax, fatty acids (e.g., stearic acid) and metal salts thereof, pigments such as carbon black, flame retardants, and the like may be blended alone or in admixture.

The epoxy resin compositions of the invention may be prepared by mixing and agitating predetermined amounts of the necessary components uniformly, and milling the mixture in milling means preheated at 70° to 95° C., for example, a kneader, roll mill and extruder, followed by cooling and comminution. The order of mixing the components is not critical.

The compositions of the invention are advantageously applicable in encapsulating various types of semiconductor device including DIP, flat pack, PLCC and SO types. The compositions can be molded by conventional methods including transfer molding, injection molding, and casting. Most often, the epoxy resin compositions are molded at a temperature of about 150° to about 180° C. and post cured at a temperature of about 150° to about 180° C. for about 2 to about 16 hours.

Due to the fluorinated organic silicon compound of formula (1) blended therein, the semiconductor encapsulating epoxy resin composition of the present invention has good adhesion to frames and silicon chips and improved moisture resistance, especially after a moisture absorption and soldering test. Therefore, semiconductor devices sealed with the composition in cured state remain reliable.

EXAMPLE

Examples of the present invention are given below by way of illustration and not by way of limitation. All parts and percents are by weight.

First described is the preparation of compounds of formula (1).

Preparation 1

A 500-ml three-necked flask equipped with a condenser, dropping funnel, thermometer and magnetic stirrer was charged with 108.5 grams (0.55 mol) of 1,1,1-trifluoro-2-trifluoromethyl-3-buten-2-ol, 254.4 grams (2.75 mol) of chloromethyloxirane, and 18.7 grams (0.055 mol) of tetrabutyl ammonium hydrogen sulfate. With stirring, the flask was heated to 70° C. Then 146.7 grams (0.55 mol) of a 14% sodium hydroxide aqueous solution was added dropwise over about 1.5 hours and agitation continued for a further 30 minutes. The reaction solution was allowed to cool down to room temperature, whereupon the organic phase was separated from the aqueous phase, washed with water twice, and then dried over 30.0 grams of anhydrous sodium sulfate. After excess chloromethyloxirane was distilled off, vacuum distillation yielded 89.4 grams of the fluorinated allyl glycidyl ether of formula (2a). It has a boiling point of 81°–82° C./65 Torr and a yield of 65.0%.

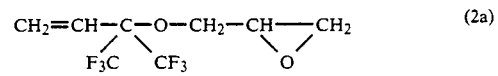

Next, a 100-ml pressure-resistant stainless steel cylinder was charged with 25.0 grams (0.10 mol) of the compound of formula (2a), 14.7 grams (6.0×10$^{-5}$ mol) of (CH$_3$O)$_3$SiH, and 0.024 grams (6.0×10$^{-5}$ mol) of Rh(CH$_2$COCHCOCH$_2$)$_3$ and heated at 135° C. for 10 hours. Then 7.3 grams (0.06 mol) of (CH$_3$O)$_3$SiH and 0.024 grams (6.0×10$^{-5}$ mol) of Rh(CH$_2$COCHCOCH$_2$)$_3$ were added to the reactor, which was heated at 135° C. for a further 10 hours. Distillation of the reaction mixture provided 22.0 grams of a product. On analysis, it was identified to be the compound of formula (1a). The yield was 59%.

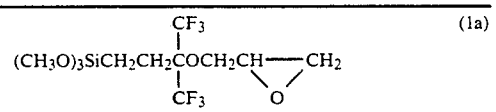

Analysis
$^1$F-NMR (CF$_3$COOH standard): 4.9 ppm(s)
$^1$H-NMR (TMS standard):

0.64~0.93 ppm(m, 2H, ≡Si—C$\underline{H}_2$—)

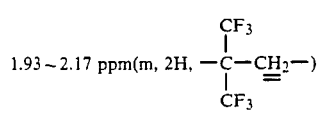

2.53~2.86 ppm(m, 2H, —C$\underline{H}$——C$\underline{H}_2$)

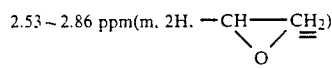

3.06~3.17 ppm(m, 1H, —C$\underline{H}$——CH$_2$)

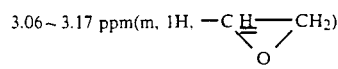

-continued 3.55 ppm(s, 9H, (C$\underline{H_3}$O)$_3$Si—)

3.61~3.79 ppm(m, 2H, —O—C$\underline{H_2}$—CH—)

IR (cm$^{-1}$):
3060(w), 2955(s), 2850(s),
1458(m), 1280(s), 1210(a),
1085(s), 827(s)

Elemental analysis:

|  | C | H | F | Si |
|---|---|---|---|---|
| Calcd. (%) | 35.48 | 4.87 | 30.61 | 7.54 |
| Found (%) | 35.02 | 4.81 | 31.15 | 7.99 |

Preparation 2

A 300-ml four-necked flask equipped with a condenser, dropping funnel, thermometer and magnetic stirrer was charged with 43.3 grams (0.208 mol) of 1,1,1-trifluoro-2-trifluoromethyl-4-penten-2-ol, 96.2 grams (1.04 mol) of epichlorohydrin, and 7.1 grams (0.021 mol) of tetrabutyl ammonium hydrogen sulfate. With stirring, the flask was heated to 85° C. Then 55.5 grams (0.208 mol) of a 15% sodium hydroxide aqueous solution was added dropwise over about 30 minutes and agitation continued at 85° C. for a further 30 minutes. The organic phase (lower layer) was separated from the reaction mixture, washed with water twice, and then dried over anhydrous sodium sulfate. Vacuum distillation of this mixture yielded 38.7 grams of a fraction having a boiling point of 88°-90° C./47 mmHg. It was identified to be the fluorinated unsaturated glycidyl ether of formula (2b). The yield was 70%.

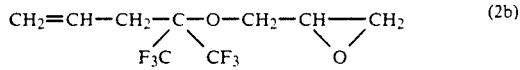
(2b)

Next, a 200-ml three-necked flask equipped with a reflux condenser, dropping funnel, thermometer and magnetic stirrer was charged with 26.4 grams (0.10 mol) of the compound of formula (2b) and 0.011 grams (2.8×10$^{-5}$ mol) of Rh(CH$_2$COCHCOCH$_2$)$_3$ and heated at 80° C. Then 17.1 grams (0.14 mol) of (CH$_3$O)$_3$SiO was added over 2 hours to the flask, which was heated at 80° C. for a further 15 hours. Distillation of the reaction mixture provided 25.5 grams of a product. On analysis, it was identified to be the compound of formula (1b). The yield was 66%.

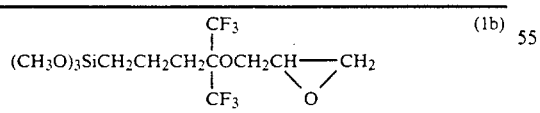
(1b)

Analysis
$^{19}$F-NMR (CF$_3$COOH standard): 4.7 ppm(s)
$^1$H-NMR (TMS standard):

0.54~0.78 ppm(m, 2H, ≡Si—C$\underline{H_2}$—)

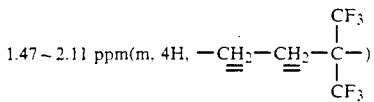

-continued 2.51~2.84 ppm(m, 2H, —C$\underline{H}$—C$\underline{H_2}$)
 \O/

3.04~3.15 ppm(m, 1H, —C$\underline{H}$—CH$_2$)
 \O/

3.55 ppm(s, 9H, (C$\underline{H_3}$O)$_3$Si—)

3.75~3.81 ppm(m, 2H, —O—C$\underline{H_2}$—CH )

IR (cm$^{-1}$):
3060(w), 2955(s), 2850(s),
1464(m), 1274(s), 1210(a),
1090(s), 818(s)

Elemental analysis:

|  | C | H | F | Si |
|---|---|---|---|---|
| Calcd. (%) | 37.30 | 5.22 | 29.50 | 7.27 |
| Found (%) | 36.98 | 5.10 | 28.85 | 7.51 |

Examples 1-10 and Comparative Examples 1-2

Semiconductor encapsulating epoxy resin compositions were prepared by uniformly melting and milling the components shown in Table 1 in a hot two-roll mill, cooling and comminuting the blends into chips.

For these compositions, the following tests (A) to (H) were carried out. The results are shown in Table 1.

(A) Spiral Flow

Using a mold according to the EMMI standard, measurement was made at 180° C. and 70 kg/cm$^2$.

(B) Flexural Strength and Flexural Modulus

Test bars of 10×4×100 mm which were molded at 180° C. and 70 kg/cm$^2$ for 2 minutes and post cured at 180° C. for 4 hours were tested according to JIS K6911.

(C) Coefficient of Linear Expansion ($\mu$) and Glass transition temperature (Tg)

Test pieces of 4 mm in diameter and 15 mm long were examined by means of a dilatometer while heating the test pieces at a rate of 5° C./min.

(D) Adhesion I

As shown in FIG. 1, a frustoconical package 2 of 10 mm in top diameter, 15 mm in bottom diameter and 5 mm high was molded on a 42-alloy plate 1 of 0.25 mm thick at 175° C. for 2 minutes and post cured at 180° C. for 4 hours. Using a push-pull gage, the force required to separate the package from the plate was measured.

(E) Moisture Resistance I

Silicone chips of 9.0×4.5×0.5 mm were bonded to plastic leaded chip carrier (PLCC) frames with 20 pins and then encapsulated with the epoxy resin compositions by molding at 180° C. for 2 minutes and post curing at 180° C. for 4 hours. The packages were allowed to stand for 48 hours in a hot humid atmosphere at 85° C. and RH 85%, then dipped in a solder bath at 260° C., and again allowed to stand for 100 hours in a hot humid atmosphere at 130° C. and RH 85%. Reported is the percentage of Al wire corroded packages/the total number of packages tested. The aluminum pattern had a line width of 5 μm.

(F) Moisture Resistance II

Silicone chips of 8.0×10.0×0.5 mm were bonded to flat packages of 10×14×2.3 mm and then encapsulated with the epoxy resin compositions by molding at 180° C. for 2 minutes and post curing at 180° C. for 4 hours. The packages were allowed to stand for 72 hours in a hot humid atmosphere at 85° C. and RH 85%, then dipped in a solder bath at 260° C., and again allowed to stand for 100 hours in a hot humid atmosphere at 121° C. and RH 100%. Reported is the percentage of Al wire corroded packages/the total number of packages tested. The aluminum pattern had a line width of 5 μm.

(G) Adhesion II

Silicone chips of 9.0×4.5×0.5 mm were bonded to 14PIN-IC frames of 42 alloy and then encapsulated with the epoxy resin compositions by molding at 180° C. for 2 minutes and post curing at 180° C. for 4 hours. The packages were allowed to stand for 24 hours in a hot humid atmosphere at 121° C. and RH 100% and then dipped for 30 seconds in a solder bath at 215° C. The adhesion between the chip and encapsulant was examined by means of a ultrasonic flaw detector Model AT 5000 (Hitachi, Ltd.) and evaluated in accordance with the following criterion.

◯: very good
X: poor (H) Water absorption

Disks of 50 mm in diameter and 3 mm thick were molded at 180° C. for 2 minutes and post cured at 180° C. for 4 hours. The disks were allowed to stand in an atmosphere at 85° C./85% RH for 24 hours before the water absorption (percent) was measured.

TABLE 1

| | | Example | | | | | |
|---|---|---|---|---|---|---|---|
| | | 1 | 2 | 3 | 4 | 5 | 6 |
| Composition, parts by weight | | | | | | | |
| Epoxy resin I | (1) | 58.0 | 37.0 | 37.0 | 37.0 | 37.0 | 37.0 |
| Epoxy resin II | (2) | — | — | — | — | — | — |
| Brominated epoxy resin | (3) | 8.0 | 8.0 | 8.0 | 8.0 | 8.0 | 8.0 |
| Phenol novolak resin | (4) | 34.0 | 31.0 | 31.0 | 31.0 | 31.0 | 31.0 |
| Block copolymer | (5) | — | 24.0 | 24.0 | 24.0 | 24.0 | 24.0 |
| $Sb_2O_3$ | | 8 | 8 | 8 | 8 | 8 | 8 |
| Carbon black | | 1 | 1 | 1 | 1 | 1 | 1 |
| Cornauba wax | | 1 | 1 | 1 | 1 | 1 | 1 |
| Triphenylphosphine | | 0.7 | 0.7 | 0.7 | 0.7 | 0.7 | 0.7 |
| Ground quartz I | (6) | 550 | 550 | 550 | 550 | 550 | 550 |
| Ground quarts II | (7) | — | — | — | — | — | — |
| Coupling agent I | (8) | 1.5 | 0.5 | 1.5 | 2.5 | — | — |
| Coupling agent II | (9) | — | — | — | — | 1.5 | 2.5 |
| Coupling agent III | (10) | — | — | — | — | — | — |
| Properties | | | | | | | |
| Spiral flow, inch | | 38 | 32 | 34 | 36 | 34 | 35 |
| Flexural strength, kg/mm$^2$ | | 14.2 | 14.0 | 14.3 | 14.6 | 14.3 | 14.2 |
| Flexural modulus, kg/mm$^2$ | | 1900 | 1600 | 1600 | 1610 | 1600 | 1620 |
| μ, $10^{-1}$/°C. | | 1.1 | 1.0 | 1.0 | 1.0 | 1.0 | 1.0 |
| Tg, °C. | | 165 | 164 | 163 | 165 | 166 | 164 |
| Adhesion I, kg | | 2.0 | 2.2 | 2.4 | 2.9 | 2.4 | 3.0 |
| Moisture resistance I, % | | 0 | 0 | 0 | 0 | 0 | 0 |
| Moisture resistance II, % | | 0 | 0 | 0 | 0 | 0 | 0 |
| Adhesion II | | ◯ | ◯ | ◯ | ◯ | ◯ | ◯ |
| Water absorption, % | | 0.25 | 0.25 | 0.24 | 0.23 | 0.24 | 0.23 |

TABLE 2

| | | Example | | | | Comparative Example | |
|---|---|---|---|---|---|---|---|
| | | 7 | 8 | 9 | 10 | 1 | 2 |
| Composition, parts by weight | | | | | | | |
| Epoxy resin I | (1) | 37.0 | 37.0 | — | 37.0 | 37.0 | — |
| Epoxy resin II | (2) | — | — | 38.2 | — | — | 38.2 |
| Brominated epoxy resin | (3) | 8.0 | 8.0 | 8.0 | 8.0 | 8.0 | 8.0 |
| Phenol novolak resin | (4) | 31.0 | 31.0 | 29.8 | 31.0 | 31.0 | 29.8 |
| Block copolymer | (5) | 24.0 | 24.0 | 24.0 | 24.0 | 24.0 | 24.0 |
| $Sb_2O_3$ | | 8 | 8 | 8 | 8 | 8 | 8 |
| Carbon black | | 1 | 1 | 1 | 1 | 1 | 1 |
| Cornauba wax | | 1 | 1 | 1 | 1 | 1 | 1 |
| Triphenylphosphine | | 0.7 | 0.7 | 0.7 | 0.7 | 0.7 | 0.7 |
| Ground quartz I | (6) | — | — | 550 | 550 | 550 | 550 |
| Ground quarts II | (7) | 553 | 553 | — | — | — | — |
| Coupling agent I | (8) | 1.5 | — | 1.5 | 1.0 | — | — |
| Coupling agent II | (9) | — | 1.5 | — | — | — | — |
| Coupling agent III | (10) | — | — | — | 0.5 | 1.5 | 1.5 |
| Properties | | | | | | | |
| Spiral flow, inch | | 36 | 35 | 35 | 34 | 32 | 33 |
| Flexural strength, kg/mm$^2$ | | 14.5 | 14.8 | 15.0 | 14.8 | 14.2 | 14.3 |
| Flexural modulus, kg/mm$^2$ | | 1600 | 1590 | 1630 | 1600 | 1620 | 1630 |
| μ, $10^{-1}$/°C. | | 1.0 | 1.0 | 1.0 | 1.0 | 1.0 | 1.0 |
| Tg, °C. | | 165 | 165 | 166 | 163 | 164 | 165 |
| Adhesion I, kg | | 3.0 | 3.0 | 2.8 | 2.4 | 0.9 | 0.8 |

TABLE 2-continued

| | | | | | | |
|---|---|---|---|---|---|---|
| Moisture resistance I, % | 0 | 0 | 0 | 0 | 15 | 10 |
| Moisture resistance II, % | 0 | 0 | 0 | 0 | 30 | 15 |
| Adhesion II | ○ | ○ | ○ | ○ | X | X |
| Water absorption, % | 0.23 | 0.23 | 0.17 | 0.26 | 0.27 | 0.19 |

(1) Epoxy resin I  
 EOCN 1020-70  Epoxy equiv. 196  
 (Nippon Kayaku K.K.)

(2) Epoxy resin II  
 EOCN 7000  Epoxy equiv. 215  
 (Nippon Kayaku K.K.)

(3) Brominated epoxy resin  
 BREN-S  Epoxy equiv. 280  
 (Nippon Kayaku K.K.)

(4) Phenol novolak resin  
 KH 3488  Phenol equiv. 110  
 (Dai-Nihon Ink K.K.)

(5) Block copolymer  
 an addition reaction product of the components:

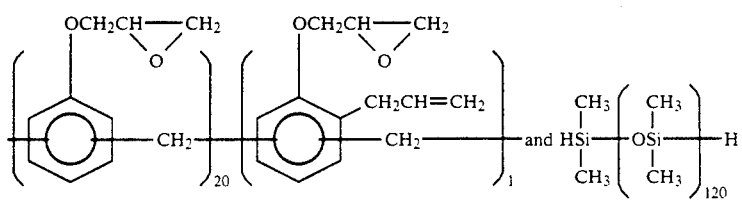

(suffixes are average values)  
epoxy equivalent 305  
organopolysiloxane content 34%

(6) Ground quartz I  
 a mixture of 500 parts of spherical silica having a mean particle size of 30 μm and containing less than 0.1% of particles having a size of larger than 75 μm and 50 parts of spherical silica having a mean particle size of 1 μm and a specific surface of 6 m²/g.

(7) Ground quartz II  
 ground quartz I surface treated with 3 parts of coupling agent I.

(8) Coupling agent I

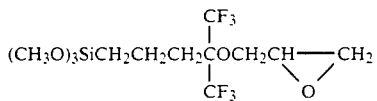

(9) Coupling agent II

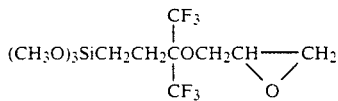

(10) Coupling agent III  
 γ-glycidoxypropyltrimethoxysilane  
 KBM403E (Shin-Etsu Chemical Co., Ltd.)

As is evident from Table 1, those epoxy resin compositions having fluorinated organic silicon compounds of formula (1) cure into products having improved adhesion and moisture resistance.

Although some preferred embodiments have been described, many modifications and variations may be made thereto in the light of the above teachings. It is therefore to be understood that within the scope of the appended claims, the invention may be practiced otherwise than as specifically described.

We claim:

1. An epoxy resin composition for semiconductor encapsulation comprising
 an epoxy resin,
 a curing agent,
 an inorganic filler, and
 a fluorinated organic silicon compound of the formula:

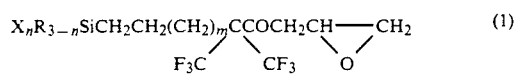

wherein X is a hydrolyzable group, R is a substituted or unsubstituted monovalent hydrocarbon group, n is an integer of 1 to 3, and m is equal to 0 or 1.

2. An epoxy resin composition according to claim 1 wherein said epoxy resin has at least two epoxy groups in a molecule.

3. An epoxy resin composition according to claim 1 wherein said curing agent is an amine curing agent, acid anhydride curing agent or phenol functional curing agent.

4. An epoxy resin composition according to claim 3 wherein said curing agent is a phenol functional curing agent and the molar ratio of epoxy group in the epoxy resin to phenolic hydroxyl group in the curing agent is in the range of from ½ to 3/2.

5. An epoxy resin composition according to claim 4, wherein said fluorinated organic silicon compound of formula (1) is selected from the group consisting of:

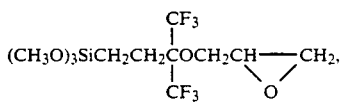

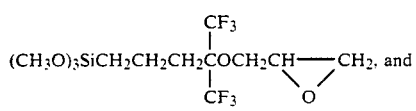

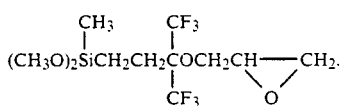

6. An epoxy resin composition according to claim 1 which contains 50 to 800 parts of the filler per 100 parts by weight of the epoxy resin and curing agent combined.

7. An epoxy resin composition according to claim 1 wherein the compound of formula (1) is blended in an amount of 0.05 to 10 parts by weight per 100 parts by weight of the epoxy resin and curing agent combined.

8. A semiconductor device encapsulated with a cured product of an epoxy resin composition as set forth in any one of claims 1 to 7.

9. An epoxy resin composition according to claim 7, wherein said fluorinated organic silicon compound of formula (1) is selected from the group consisting of:

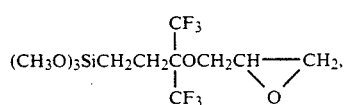

-continued

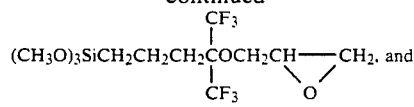

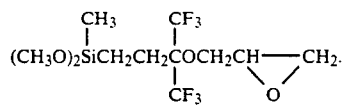

10. An epoxy resin composition according to claim 1, wherein X of formula (1) is represented by the formula $OR^1$ or $NR^2R^3$, wherein $R^1$ is an alkyl group having 1 to 10 carbon atoms, a fluoroalkyl group having 3 to 15 carbon atoms, or an alkenyl group having 2 to 5 carbon atoms, and $R^2$ and $R^3$, which may be the same or different, are each an alkyl group having 1 to 10 carbon atoms.

11. An epoxy resin composition according to claim 1, wherein R of formula (1) is an alkyl group having 1 to 10 carbon atoms, an alkenyl group having 2 to 10 carbon atoms, an aryl group having 6 to 10 carbon atoms, an aralkyl group having 7 to 15 carbon atoms, or a fluoroalkyl group having 3 to 15 carbon atoms.

12. An epoxy resin composition according to claim 10, wherein R of formula (1) is an alkyl group having 1 to 10 carbon atoms, an alkenyl group having 2 to 10 carbon atoms, an aryl group having 6 to 10 carbon atoms, an aralkyl group having 7 to 15 carbon atoms, or a fluoroalkyl group having 3 to 15 carbon atoms.

13. An epoxy resin composition according to claim 12, wherein X of formula (1) is represented by said formula $OR^1$.

14. An epoxy resin composition according to claim 12, wherein X of formula (1) is represented by said formula $NR^2R^3$.

15. An epoxy resin composition according to claim 1, wherein said fluorinated organic silicon compound of formula (1) is selected from the group consisting of:

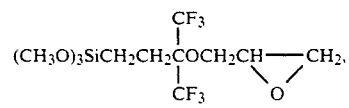

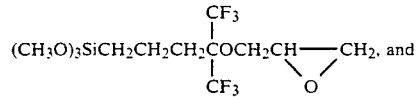

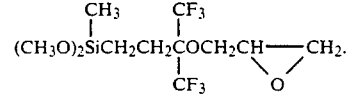

* * * * *